(12) United States Patent
Cai et al.

(10) Patent No.: US 12,292,580 B2
(45) Date of Patent: May 6, 2025

(54) OPTICAL MODULE AND MEDICAL LASER DEVICE

(71) Applicant: FOCUSLIGHT TECHNOLOGIES INC., Xi'an (CN)

(72) Inventors: Lei Cai, Xi'an (CN); Xingsheng Liu, Xi'an (CN)

(73) Assignee: FOCUSLIGHT TECHNOLOGIES INC., Xi'an (CN)

( * ) Notice: Subject to any disclaimer, the term of this patent is extended or adjusted under 35 U.S.C. 154(b) by 488 days.

(21) Appl. No.: 17/912,395

(22) PCT Filed: Aug. 11, 2020

(86) PCT No.: PCT/CN2020/108508
§ 371 (c)(1),
(2) Date: Sep. 16, 2022

(87) PCT Pub. No.: WO2022/021476
PCT Pub. Date: Feb. 3, 2022

(65) Prior Publication Data
US 2023/0136630 A1    May 4, 2023

(30) Foreign Application Priority Data
Jul. 31, 2020  (CN) .......................... 202010757215.3

(51) Int. Cl.
*G02B 27/09*   (2006.01)
*A61B 18/20*   (2006.01)

(52) U.S. Cl.
CPC .......... *G02B 27/0927* (2013.01); *A61B 18/20* (2013.01); *G02B 27/0916* (2013.01);
(Continued)

(58) Field of Classification Search
CPC ...... G02B 27/09; G02B 27/12; G02B 27/123; G02B 27/14; G02B 3/06;
(Continued)

(56) References Cited

U.S. PATENT DOCUMENTS

2002/0191301 A1* 12/2002 Tanaka ............... G02B 27/0977
    257/E27.111
2005/0219493 A1* 10/2005 Oshida ............... G02B 19/0014
    355/53

(Continued)

*Primary Examiner* — Ricky L Mack
*Assistant Examiner* — Journey F Sumlar
(74) *Attorney, Agent, or Firm* — IPro, PLLC (57) ABSTRACT

The present application provides an optical module and a medical laser device, belonging to the technical field of applying the light spot, comprising a first lens, a second lens and an array lens arranged in sequence along the main optical axis, wherein the first lens shapes a beam along the first direction of the main optical axis, the second lens shapes the beam along the second direction of the main optical axis, the array of array lenses is arranged along the second direction of the main optical axis. The laser beam enters the second lens after passing through the first lens, and the second lens diffuses the laser beam along the second direction of the main optical axis, and after the laser beam is converted from a Gaussian distribution to a flat-top distribution in the second direction, the laser beam is emitted through the array lens.

19 Claims, 11 Drawing Sheets

(52) U.S. Cl.
CPC ..... *G02B 27/0933* (2013.01); *G02B 27/0961* (2013.01); *G02B 27/0977* (2013.01); *A61B 2018/20359* (2017.05); *A61B 2018/20553* (2017.05)

(58) Field of Classification Search
CPC .......... G02B 27/095–27/0966; G02B 27/0977; G02B 27/0938; G02B 3/0068
See application file for complete search history.

(56) References Cited

U.S. PATENT DOCUMENTS

2006/0222041 A1* 10/2006 Moriwaka .......... G02B 27/0961
372/101
2009/0154318 A1* 6/2009 Noehte .............. G02B 27/0081

\* cited by examiner

OPTICAL MODULE AND MEDICAL LASER DEVICE

CROSS-REFERENCE TO RELATED APPLICATIONS

The present application claims the priority of the Chinese patent application filed with the Chinese Patent Office on Jul. 31, 2020, with the application number CN202010757215.3, titled as "Optical Module and Medical Laser Device", the entire contents of which are incorporated herein by reference.

TECHNICAL FIELD

The present application relates to the technical field of applying light spots, in particular, to an optical module and a medical laser device.

BACKGROUND ART

In the application of a laser spot, it is necessary to convert the original Gaussian distribution emitted by the semiconductor laser into a flat-top distribution. Currently, a method is commonly used, wherein plural lens components are used, so that the overall volume of the system is larger. Moreover, in order to obtain a large-area point/line spot, the existing dot matrix technology needs to use a single-point scanning method, which is inefficient.

Although the array lens has the effect of cutting light into points/lines, in the application of laser medical treatment, the direct laser distribution is Gaussian distribution, and the axial size is small, and it cannot be directly converted by the lens array.

SUMMARY

The purpose of the present application is to provide an optical module and a medical laser device, which can realize the conversion of the original Gaussian distribution of the laser beam into a flat-top distribution, and the optical module is small in volume.

Embodiments of the present application are implemented as follows.

An aspect of the embodiments of the present application provides an optical module, which comprises a first lens, a second lens and an array lens arranged in sequence along a main optical axis, wherein the first lens shapes a beam along a first direction of the main optical axis, the second lens shapes the beam along a second direction of the main optical axis, the array lens has an array arranged along the second direction of the main optical axis, and a laser beam enters the second lens after passing through the first lens, the second lens diffuses the laser beam along the second direction and converts the laser beam from a Gaussian distribution to a flat-top distribution in the second direction, and then the laser beam exits through the array lens, wherein the first direction and the second direction are perpendicular to each other.

Optionally, the first lens is an ellipsoid lens, and the second lens is a hyperboloid lens.

Optionally, it further comprises a third lens located between the second lens and the array lens, wherein the third lens shapes a beam along a second direction of the main optical axis.

Optionally, the array lens comprises a plurality of first arc surfaces or a sawtooth surface continuously formed along the second direction, and the first arc surfaces or the sawtooth surface are located on an incident surface or an exiting surface of the array lens.

Optionally, the incident surface of the array lens is a flat surface, a convex surface or a concave surface, and the exiting surface of the array lens is formed of a plurality of the first arc surfaces or the sawtooth surface; or, the incident surface of the array lens is formed of a plurality of the first arc surfaces or a sawtooth surface, and the exiting surface of the array lens is a flat surface, a convex surface or a concave surface.

Optionally, the array lens further comprises a plurality of second arc surfaces or a sawtooth surface arranged along the first direction, and the second arc surfaces or the sawtooth surface are located on an incident surface or the exiting surface of the array lens.

Optionally, the incident surface or the exiting surface of the array lens comprises a plurality of first arc surfaces continuously formed along the second direction, and the incident surface or the exiting surface of the array lens further comprises a plurality of second arc surfaces continuously arranged along the first direction on the basis of the plurality of first arc surfaces; or the incident surface of the array lens is a sawtooth surface arranged along the first direction, and the exiting surface of the array lens is formed of a plurality of the first arc surfaces arranged along the second direction; or the incident surface of the array lens is formed of a plurality of the first arc surfaces arranged along the second direction, and the exiting surface of the array lens is a sawtooth surface arranged along the first direction; or the incident surface of the array lens is a sawtooth surface, and the exiting surface of the array lens is a sawtooth surface.

Optionally, the array lens comprises a first array lens and a second array lens, and the first arc surfaces or the sawtooth surface are located on an incident surface or an exiting surface of the first array lens, and/or the incident surface or the exiting surface of the second array lens.

Optionally, the array lens is an array reflecting mirror, and a plurality of first arc surfaces or sawtooth disposed along the second direction are continuously formed on the reflecting surface of the array reflecting mirror.

Optionally, the array lens can reciprocate along a sawtooth arrangement direction, or rotate along a main optical axis direction.

Optionally, tooth surfaces of the sawtooth have curvature.

Optionally, the first lens is movable along a main optical axis direction to change a light output range of the exiting surface of the array lens.

Optionally, a reflecting mirror is further provided between the second lens and the third lens.

Optionally, the reflecting mirror is rotatable along the main optical axis, and a rotation angle of the reflecting mirror is 0°-90°, so as to scan a light spot within the rotation angle.

Another aspect of the embodiments of the present application provides a medical laser device, comprising a casing which is therein provided with the laser and the optical module mentioned above, that is arranged in an exiting direction of the laser.

Optionally, the casing comprises a handle and a lens barrel, the laser is arranged in the handle, the optical module is arranged in the lens barrel, the lens barrel and the handle are detachably connected with each other; and the lens barrel comprises a replaceable head, the array lens is located in the replaceable head, and the replaceable head and the lens barrel are detachably connected.

Optionally, it further comprises a first motor and/or a second motor, wherein the first motor and the second motor are respectively connected to the first lens and the array lens.

The beneficial effects of the embodiments of the present application comprise the follows.

The optical module is provided by the embodiments of the present application, wherein a first lens, a second lens and an array lens are arranged in sequence along the main optical axis. The first lens compresses, converges and collimates the light beam emitted from the light source. The laser beam emitted from the light source is converted from Gaussian light to flat-top light through the second lens. The exiting surface of the array lens is configured to emit light and cut the light spot. The first lens shapes the light beam along the first direction of the main optical axis, and the second lens shapes the light beam along the second direction of the main optical axis. The array of the array lens is arranged along the second direction of the main optical axis. The first lens, the second lens and the array lens, which are combined and matched, are configured so that the laser beam enters the second lens after passing through the first lens. The second lens expands the laser beam, converts the Gaussian distribution of the laser beam into a flat-top distribution, and then it is emitted through the array lens. By arranging three optical elements, the laser beam can be converted from the original Gaussian distribution to the flat-top distribution, making the optical module small in size.

BRIEF DESCRIPTION OF DRAWINGS

In order to illustrate the technical solutions of the embodiments of the present application more clearly, the drawings needed to be used in the embodiments will be briefly introduced below. It should be understood that the following drawings only show some embodiments of the present application, and therefore it should not be regarded as a limitation on the scope. For those skilled in the art, other related drawings can also be obtained according to these drawings without any creative efforts.

REFERENCE NUMBERS

100—first lens; 201—second lens; 202—third lens; 300—array lens; 400—reflecting mirror; 501—laser; 502—heat sink; 503—handle; 504—spacer; 505A—first motor; 505B—second motor; 505C—third motor; 506—lens barrel; 5061—replaceable head.

DETAILED DESCRIPTION

In order to make the purposes, technical solutions and advantages of the embodiments of the present application clearer, the technical solutions in the embodiments of the present application will be clearly and completely described below with reference to the drawings in the embodiments of the present application. Obviously, the described embodiments are some, but not all, of embodiments of the present application. Generally, the components of the embodiments of the present application described and illustrated in the drawings herein may be arranged and designed in a variety of different configurations.

Thus, the following detailed description of the embodiments of the present application provided in the drawings is not intended to limit the scope of the present application as claimed, but is merely representative of selected embodiments of the present application. Based on the embodiments of the present application, all other embodiments obtained by those skilled in the art without creative efforts shall fall within the protection scope of the present application.

It should be noted that similar reference numbers and letters refer to similar items in the following drawings, and thus once an item is defined in one drawing, it is not required to further define and explain it in subsequent drawings.

Figures 1, 2:
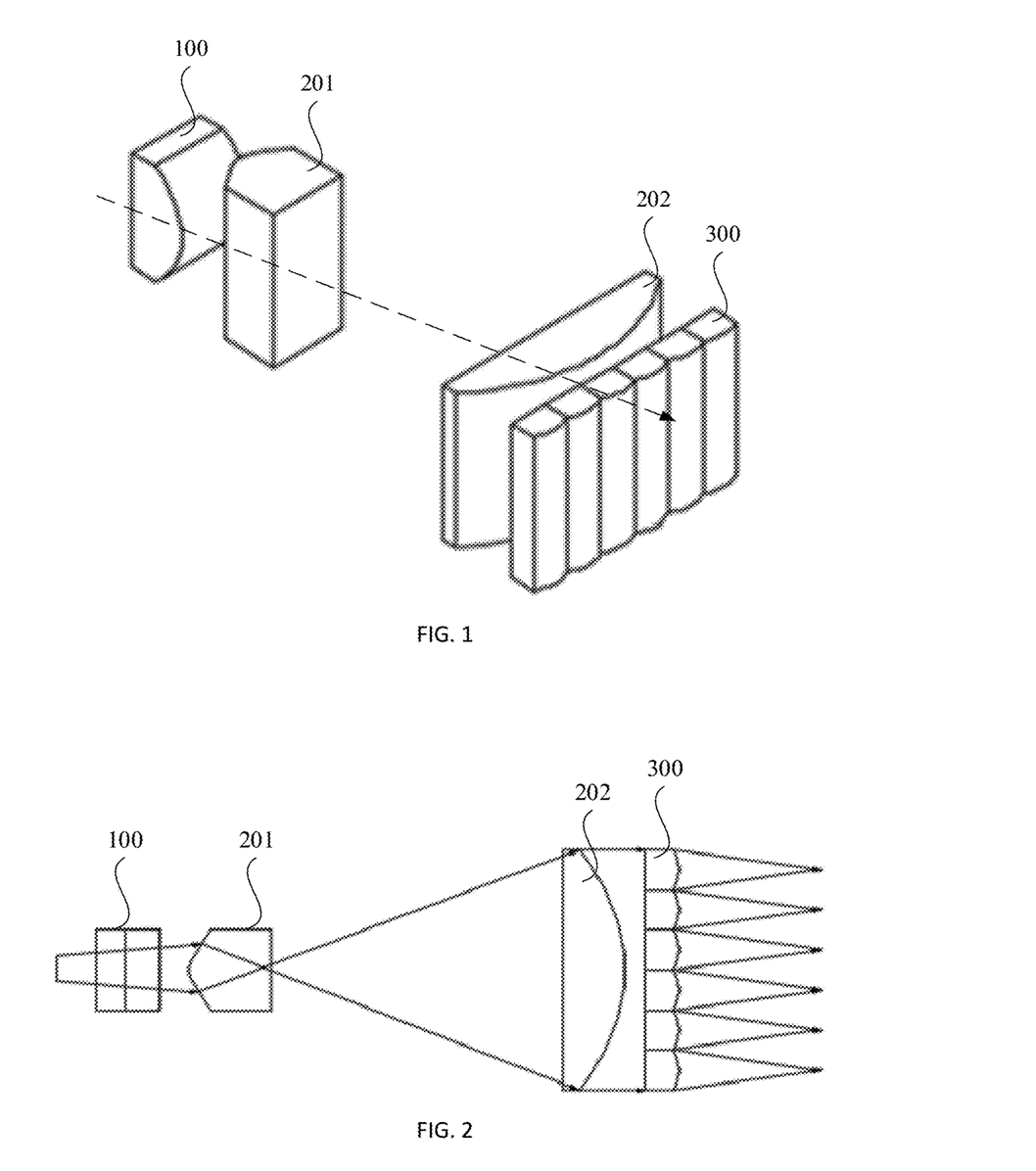
FIG. 1 is the first structural schematic diagram of a slow axis of an optical module provided by an embodiment of the present application.
FIG. 2 is the first optical path diagram of a slow axis of an optical module provided by an embodiment of the present application.

Referring to FIG. 1, this embodiment provides an optical module, which comprises a first lens 100, a second lens 201, a third lens 202 and an array lens 300 arranged in sequence along the main optical axis, wherein the first lens 100 shapes the light beam along the first direction of the main optical axis, the second lens 201 shapes the light beam along the second direction of the main optical axis, and the third lens 202 shapes the light beam along the second direction of the main optical axis. The array of the array lens 300 is arranged along the second direction of the main optical axis. The laser beam enters the second lens 201 after passing through the first lens 100. The second lens 201 diffuses the laser beam, and converts the Gaussian distribution of the laser beam into a flat-top distribution, and then it is exited through the array lens 300.

The laser light emitted from the light source passes through the first lens 100, the second lens 201, the third lens 202 and the array lens 300 in sequence. The light source, the first lens 100, the second lens 201, the third lens 202 and the array lens 300 are each on the optical axis.

When the light source is a laser light source, if the first direction is the fast axis, the first lens 100 can be a fast axis cylindrical lens, the second lens 201 can be a slow axis cylindrical lens, and the third lens 202 can be a slow axis cylindrical lens, and the array direction of the array lens 300 is arranged along the slow axis direction.

When the first direction is the slow axis, the first lens 100 is a slow axis cylindrical lens, the second lens 201 is a fast axis cylindrical lens, the third lens 202 is a fast axis cylindrical lens, and the array direction of the array lens 300 is arranged along the fast axis direction.

Furthermore, the first lens 100 is an ellipsoidal surface lens, that is, when the first lens 100 is a fast-axis cylindrical lens, it can be a fast-axis ellipsoidal surface lens, and when the first lens 100 is a slow-axis cylindrical lens, it can be a slow-axis ellipsoidal surface lens.

The second lens 201 is a hyperboloid lens, and its incident surface is a hyperboloid, so that the single lens not only realizes the expansion of the light beam, but also realizes the conversion from Gaussian light to flat-top light, which simplifies the optical structure.

The array of the array lens 300 is arranged along the second direction of the main optical axis, that is, when the second lens 201 is a slow-axis cylindrical lens, the array direction of the array lens 300 is arranged along the slow-axis direction; and when the second lens 201 is a fast-axis cylindrical lens, the array direction of the array lens 300 is arranged along the fast axis direction.

The fast axis and the slow axis of each lens in the optical module are interchangeable. As shown in FIG. 1, the present embodiment is specifically described, wherein the first lens 100 is a fast-axis cylindrical lens, the second lens 201 is a slow-axis hyperboloid mirror, and the third lens 202 is a slow-axis cylindrical lens. The exiting surface of the first lens 100 is a convex surface, the incident surface of the second lens 201 is a hyperboloid, and the exiting surface of the third lens 202 is a convex surface. The optical path diagram of it is shown in FIG. 2.

Figure 3:
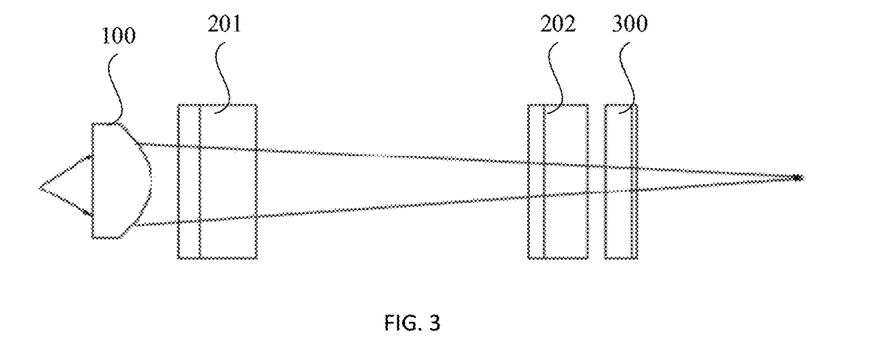
FIG. 3 is a structural schematic diagram of a fast axis of an optical module provided by an embodiment of the present application.

When the fast and slow axes are interchanged, that is, the first lens 100 is a slow-axis cylindrical lens, the second lens 201 is a fast-axis hyperboloid lens, and the third lens 202 is a fast-axis cylindrical lens. The optical path diagram of it is shown in FIG. 3.

The function of the first lens 100 is to compress, gather and collimate the light beam emitted by the light source, and the laser beam emitted by the light source is expanded along a single direction, i.e., the fast axis or the slow axis, through the second lens 201, and realizes the conversion from the Gaussian light to the flat-top light. The third lens 202 collimates the light beam and completes the correction of the edge beam at the same time. The exiting surface of the array lens 300 is configured to emit light and cut the light spot. The light beam, which is output after passing through the first lens 100, the second lens 201 and the third lens 202 in sequence, is cut into a light-spot combination of points and/or lines, on the slow axis, so as to form a light spot in the light exiting direction.

This embodiment provides the optical module, wherein a first lens 100, a second lens 201 and an array lens 300 are arranged in sequence along the main optical axis. The first lens 100 compresses, converges and collimates the light beam emitted by the light source. The laser beam output from the light source is converted from Gaussian light to flat-top light through the second lens 201. The exiting surface of the array lens 300 is configured to emit light and cut the light spot. The first lens 100 shapes the beam along the first direction of the main optical axis, and the second lens 201 shapes the beam along the second direction of the main optical axis. The array of the array lenses 300 is arranged along the second direction of the main optical axis. The first lens 100, the second lens 201 and the array lens 300, which are combined and matched, are configured so that the laser beam enters the second lens 201 after passing through the first lens 100. The second lens 201 expands the laser beam, converts the Gaussian distribution of the laser beam into a flat-top distribution, and then it is exited through the array lens 300. By arranging three optical elements, it can be realized that the original Gaussian distribution of the laser beam is converted into a flat-top distribution, so that the optical module is small in volume.

The optical module provided in this embodiment can also emit light spots of different shapes.

When an existing optical module forms a light spot, one optical module can only output light spots of a single form. For example, the output light spot can only be one of a single-point light spot, point-column light spots, point-matrix light spots, a line light spot, a surface light spot or a strip light spot. In this way, the optical module outputting a single light spot is only suitable for one industry demand. However, if a new demand arises, a new optical system is required to meet the new demand. While the single light spot output by the existing optical module can only solely corresponds to the new demand, for satisfying the use. In the case of cross-industry application, the original optical module cannot be applied to the needs of the new industry and thus fails. If it is the cross-industry application, a new set of optical modules needs to be redesigned. Compared with the original optical module, the individual optical components are changed greatly, and the overall structure of the original optical module will be changed, with high implementation cost, and the changed one can only be used in the original industry. Therefore, such an optical module has poor applicability, the cost of modification is high, and the light spots cannot be converted to each other. Once a new demand arises, the original optical module will fail, and the applicability is poor; and the light spot cannot be changed during the scanning process, with the scanning form being single.

On this basis, the optical module provided by the present application can form the light spots with various shapes, such as, row points, array points, the line shape, the plane shape or the strip shape, etc., by slightly adjusting the optical elements in this optical module. The light spots are in the diversified forms and can be converted between each other, with strong applicability, and can be used for cross-industry output, adapting to different needs, with powerful functions, high flexibility, low cost, small size, simple structure, and can be used in medical beauty (skin rejuvenation, fine hair removal and dissolving of fattiness). The matrix output is used in 3D recognition, active scanning source and laser printing and other fields.

When the light output range of the exiting surface of the array lens 300 is changed, the light spots formed by the output are changed in various ways, so as to output light spots of different shapes.

By changing the light output range of the exiting surface of the array lens 300, light spots of different shapes can be emitted, so that one optical module can achieve the purpose of converting the light spots. In this way, in practical application, this optical module can be applied across industry, with high applicability, and one optical module can be used in different occasions to meet different needs.

Specifically, the light spot conversion (transformation) is realized through the following embodiments.

The array lens 300 comprises a plurality of first arc surfaces or a sawtooth surface continuously formed along the second direction, and the first arc surfaces or the sawtooth surface are located on the incident surface or the exiting surface of the array lens 300.

The array lens 300 further comprises a plurality of second arc surfaces or a sawtooth surface arranged along the first direction, and the second arc surfaces or the sawtooth surface are located on the incident surface or the exiting surface of the array lens.

Exemplarily, as shown in FIG. 1, the exiting surface of the array lens 300 comprises a plurality of first arc surfaces continuously formed along the second direction, and the first arc surfaces are convex toward the light exiting direction, so that the exiting surface of the array lens 300 forms a pattern of plural connected strips, the light spot of the stripe shape is emitted.

Figure 4:
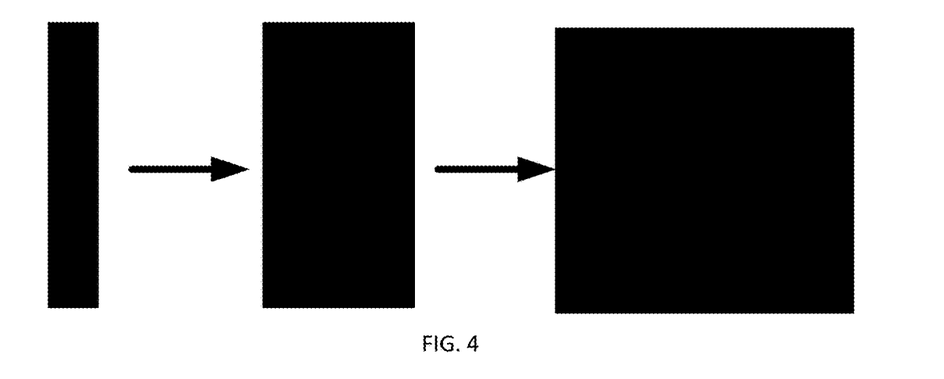
FIG. 4 is the first shape diagram of the slow axis output light spot of the optical module provided by the embodiment of the present application.

As shown in FIGS. 1 and 2, the second lens 201 is a slow-axis cylindrical lens, and the first direction is the slow-axis direction, that is, a plurality of first arc surfaces are formed continuously along the slow-axis direction on the exiting surface of the array lens 300, to emit the stripe shape light spot shown in FIG. 4.

The incident surface of the array lens 300 is a flat, convex or concave surface, and the exiting surface of the array lens 300 is formed of a plurality of first arc surfaces or a sawtooth surface. Or, the incident surface of the array lens 300 is formed of a plurality of first arc surfaces or a sawtooth surface, and the exiting surface of the array lens 300 is a flat, convex or concave surface.

Figure 5:
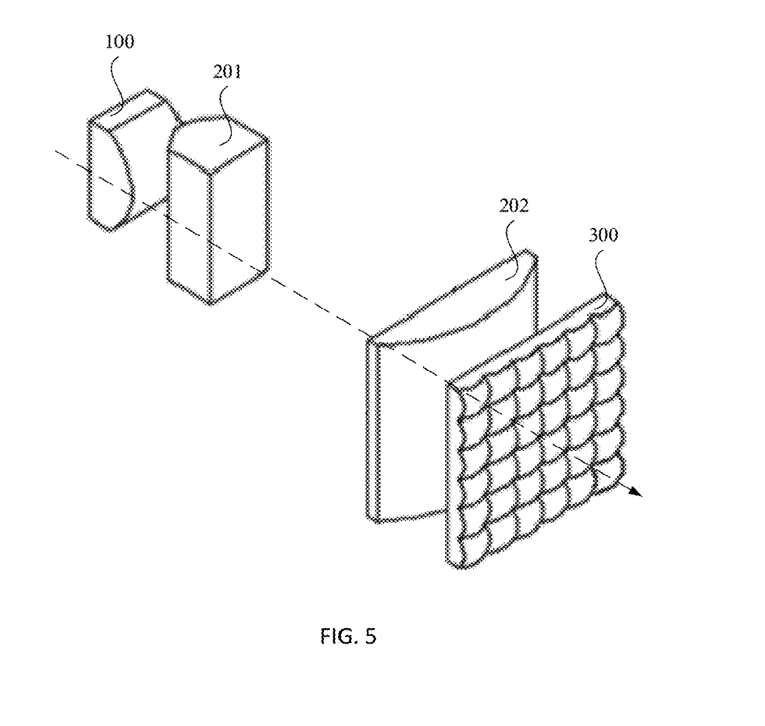
FIG. 5 is the second structural schematic diagram of the slow axis of the optical module provided by the embodiment of the present application.
Figure 14:
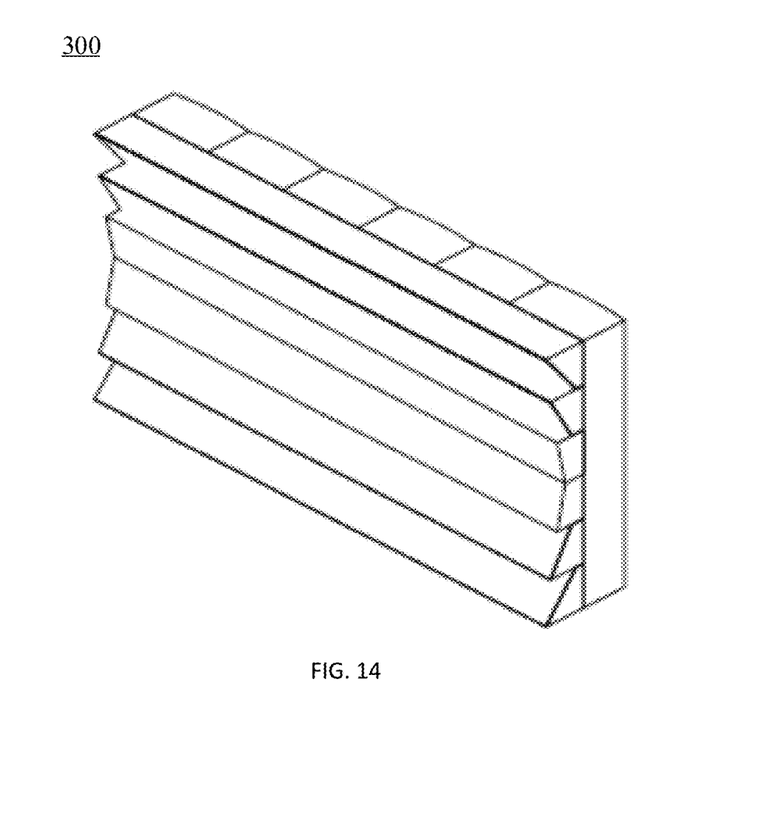
FIG. 14 is a structural schematic diagram of an array lens of an optical module provided by an embodiment of the present application.
Figure 15:
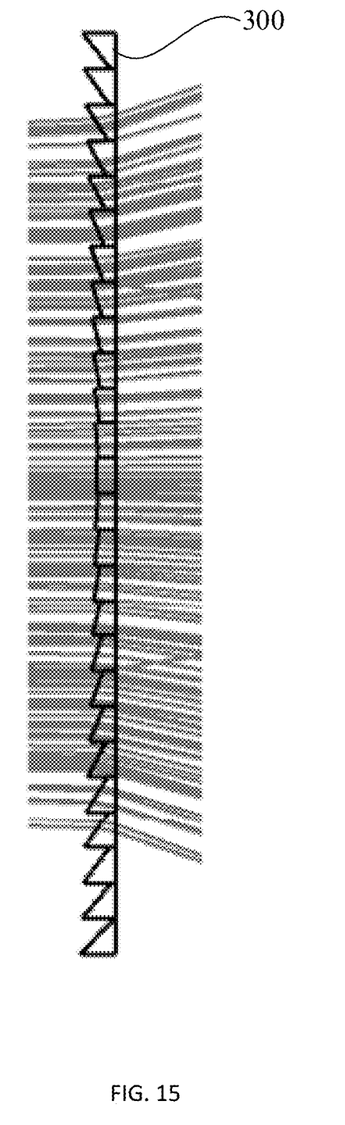
FIG. 15 is an optical path diagram of an array lens of an optical module provided by an embodiment of the present application.
Figure 16:
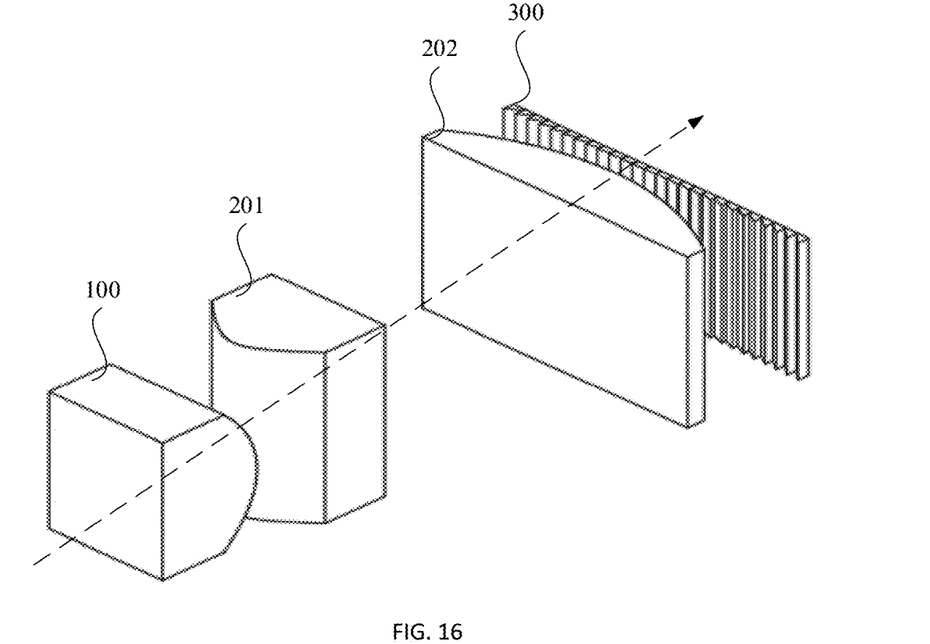
FIG. 16 is the fourth structural schematic diagram of the slow axis of the optical module provided by the embodiment of the present application.
Figure 19:
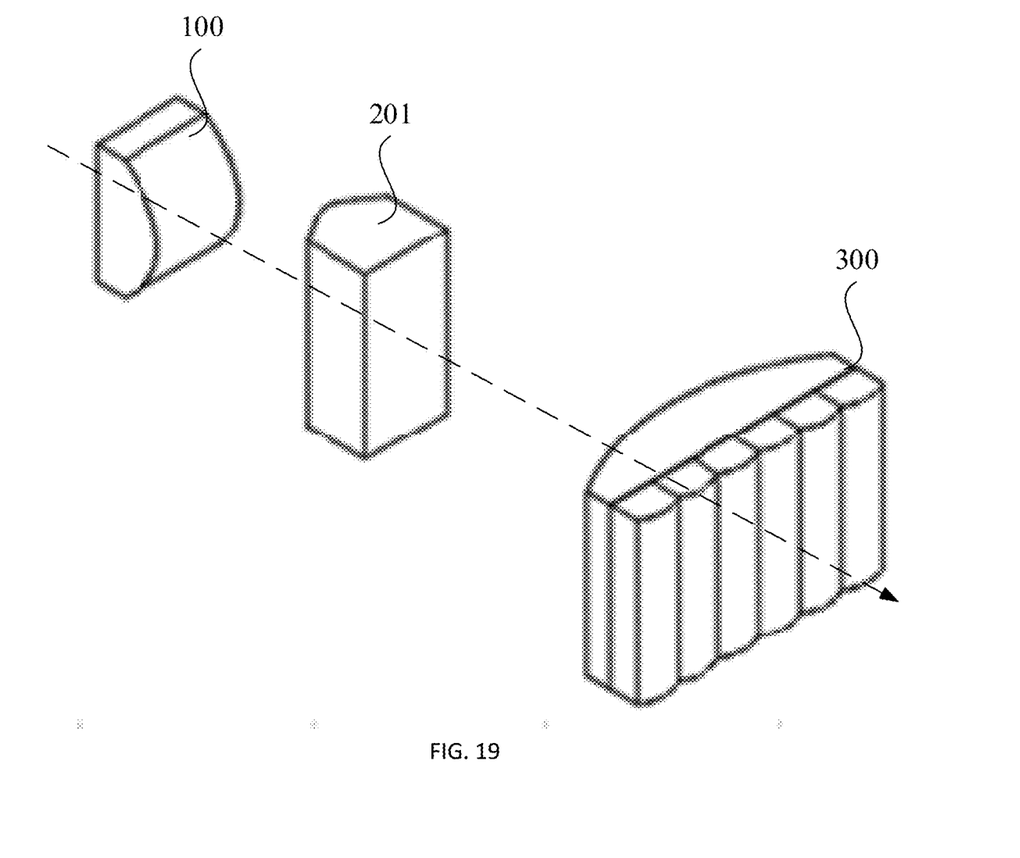
FIG. 19 is the sixth structural schematic diagram of the slow axis of the optical module provided by the embodiment of the present application.

Exemplarily, the incident surface of the array lens 300 can be a flat surface as shown in FIG. 1 and FIG. 5. The incident surface of the array lens 300 can also be a sawtooth surface as shown in FIG. 14. As shown in FIG. 16, the incident surface is a sawtooth surface. The sawtooth of the incident surface are arranged along the second direction. The light beam emitted from the exiting surface of the third lens 202 is cut into a two-dimensional point array as shown in FIG. 15 to form an array-point light-spot distribution of angular space. The third lens 202 can also be integrated with the array lens 300, that is, when the incident surface of the array lens 300 is a convex surface as shown in FIG. 19, it can be regarded as the third lens 202 being capable of being integrated with the array lens 300. In this way, the same exiting effect can be achieved, but the number of the optical components of the optical module is reduced, so that the structure of the optical module is simpler.

The incident surface or exiting surface of the array lens 300 comprises a plurality of first arc surfaces formed continuously along the second direction. The incident surface or the exiting surface of the array lens 300 further includes a plurality of second arc surfaces continuously arranged along the first direction, on the basis of the plurality of first arc surfaces.

Exemplarily, as shown in FIG. 5, the exiting surface of the array lens 300 comprises a plurality of first arc surfaces formed continuously along the second direction, and the exiting surface of the array lens 300 also comprises a plurality of second arc surfaces continuously arranged along the first direction, on the basis of the plurality of first arc surfaces, so that the exiting surfaces of the array lens 300 form a plurality of intersecting and perpendicular grids, wherein the exiting surfaces of the plurality of grids are also convex toward the light outgoing direction. Therefore, the exiting surfaces of the array lens 300 form convex parts of the array, so as to emit the row-point light spot or the array-point light spot.

The first arc surface and the second arc surface intersect to each other, to form a grid-like exiting surface. Each grid can emit one point light spot correspondingly, and the entire optical module emits the array-point light spot.

Figure 6:
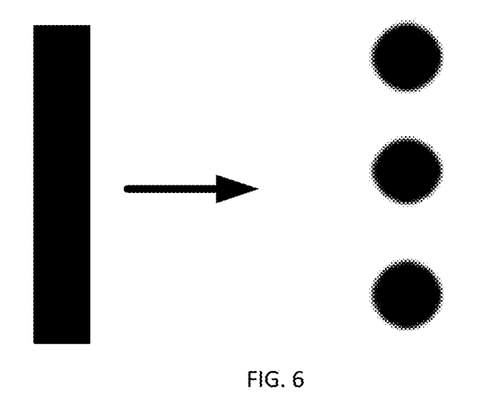
FIG. 6 is the second shape diagram of the slow axis output light spot of the optical module provided by the embodiment of the present application.

When the exiting surface forms a second arc surface on the basis of forming the first arc surface, as shown in FIG. 6, the emitted light spot can be changed from the original strip-shape light spot to a single-row point light spot.

Figure 17:
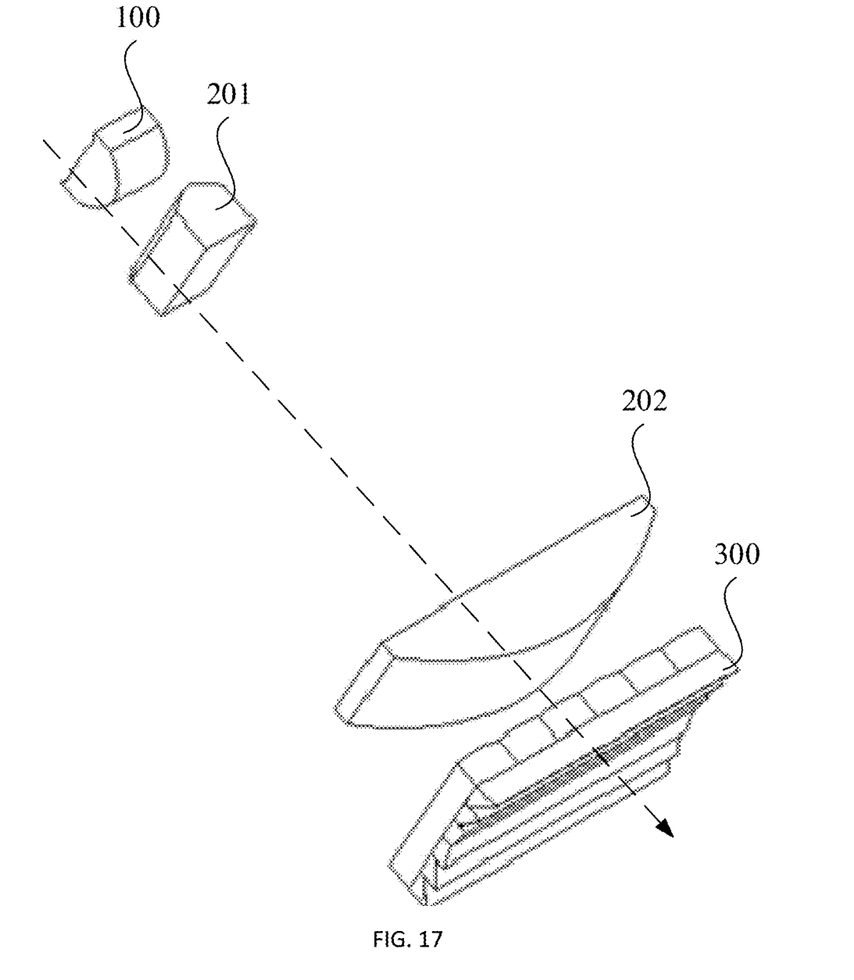
FIG. 17 is the fifth structural schematic diagram of the slow axis of the optical module provided by the embodiment of the present application.

The surface type of the incident surface and the surface type of the exiting surface of the array lens 300 can also be interchanged with each other. As shown in FIG. 5 above, the exiting surface forms grids in the arrangement, and alternatively, they can also be set on the incident surface. As shown in FIG. 17, the incident surface of the array lens 300 includes a plurality of first arc surfaces continuously formed along the second direction. The first arc surface is convex toward the direction of the light source. The exiting surface of the array lens 300 is a sawtooth surface. The sawtooth of the sawtooth surface are arranged along the first direction.

It is also possible that the incident surface of the array lens 300 is a sawtooth surface arranged along the first direction, and the exiting surface of the array lens 300 is formed of a plurality of first arc surfaces arranged along the second direction.

Alternatively, as shown in FIG. 16, the incident surface of the array lens 300 is a sawtooth surface, and the exiting surface of the array lens 300 can also be a sawtooth surface. At this time, the sawtooth surfaces can be arranged along the first direction, and can also be arranged along the second direction.

The varied light spots are formed by exchanging the incident surface and the exiting surface of the array lens 300.

The array lens 300 may also be an array reflecting mirror, and a plurality of first arc surfaces or sawtooth are continuously formed on the reflecting surface of the array reflecting mirror along the second direction. The sawtooth are arranged in the second direction.

Figure 18:
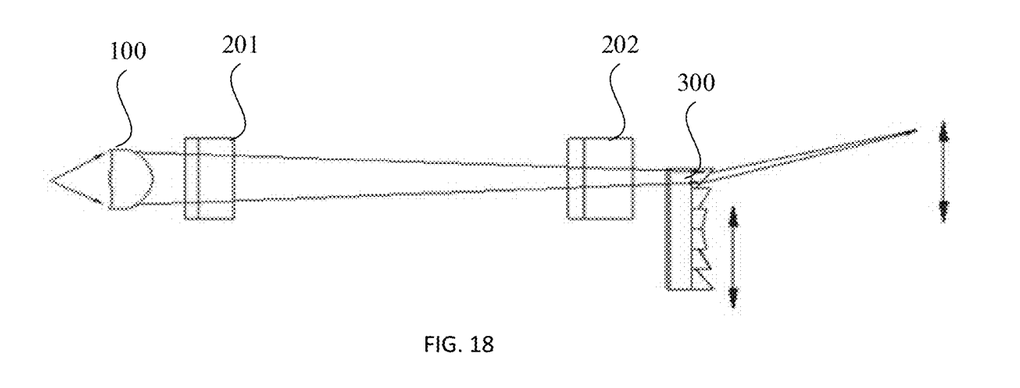
FIG. 18 is the second structural schematic diagram of the fast axis of the optical module provided by the embodiment of the present application.

Furthermore, the array lens 300 can reciprocate along the sawtooth arrangement direction, or rotate along the main optical axis direction. As shown in FIG. 18, in the fast axis direction, that is, the first lens 100 is a slow axis cylindrical lens, the second lens 201 is a fast axis cylindrical lens, the third lens 202 is a fast axis cylindrical lens, and the array direction (i.e., the array direction of the sawtooth) of array lens 300 is arranged along the fast axis direction. The array lens 300 can reciprocate along the sawtooth arrangement direction to change the light output range of the array lens 300 to form a varied light spot.

It is also possible that the array lens 300 can be separated into two lens arrays, which respectively have a plurality of first arc surfaces and a sawtooth surface that are each continuously formed along the first direction and are perpendicular to each other. That is to say, the array lens 300 comprises a first array lens and a second array lens, and the first arc surfaces or sawtooth surface are located on the incident surface or the exiting surface of the first array lens, and/or the incident surface or the exiting surface of the second array lens.

That is to say, the first arc surfaces or the sawtooth surface is located on the incident surface of the first array lens, or the first arc surfaces or the sawtooth surface are located at the exiting surface of the first array lens, or the first arc surfaces or sawtooth surface are located on the incident surface of the second array lens, or the first arc surfaces or the sawtooth surface are located on the exiting surface of the second array lens, or the incident surface and the exiting surface of the first array lens, and the incident surface and the exiting surface of the second array lens can be any one of the first arc surfaces or the sawtooth surface, and the first arc surfaces and the sawtooth surface can be randomly combined and arranged on the incident surface or the exiting surface of the two array lenses.

Exemplarily, as shown in FIG. 17, the incident surface of the first array lens comprises a plurality of first arc surfaces continuously formed along the second direction. The first arc surfaces are convex toward the light source, and the exiting surface of the second array lens is the sawtooth surface. The sawtooth arrangement direction of the sawtooth surface is perpendicular to the second direction.

Herein, exemplarily, as shown in FIG. 18, the tooth surfaces of the sawtooth have curvature.

The first lens 100 is movable along the main optical axis to change the light output range of the exiting surface of the array lens 300. When the light output ranges of the exiting surfaces of the array lens 300 are different, the shapes of the light spots formed are also different.

By moving the first lens 100 along the main optical axis, the distance between the first lens 100 and the light source is changed, and meanwhile the distance between the first lens 100 and the second lens 201 is also changed accordingly, so that after the light beam emitted by the light source passes through the first lens 100, the light output range of the light beam changes, and finally the different light spots can be formed through the exiting surface of the array lens 300.

For example, the optical module shown in FIG. 2 can emit a strip-shape light spot as shown in FIG. 4. When the distance between the first lens 100 and the light source decreases, that is, the distance between the first lens 100 and the second lens 201 increases, after the light source passes through the first lens 100, the light output range of the light increases. The area of the strip-shape light spot originally formed by the exiting surface of the array lens 300 is increased, and gradually it is changed into a rectangular light spot or even a square light spot.

As shown in FIG. 6, the distance between the first lens 100 and the light source gradually increases, the light output range gradually decreases, and the originally formed strip-shape light spot can be changed to a row-point light spot.

Figure 7:
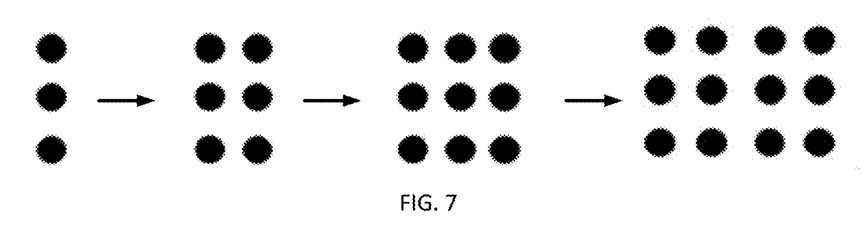
FIG. 7 is the third shape diagram of the slow axis output light spot of the optical module provided by the embodiment of the present application.

As shown in FIG. 7, along with the distance between the first lens 100 and the light source being gradually decreased, the light output range gradually increases, and the originally emitted single-row point light spot gradually become the multi-row point light spot, i.e., the array light spot.

The smaller the distance between the first lens 100 and the light source is, the larger the light output range of the light is after the light source passes through the first lens 100, and the larger the formed light spot range is.

Figure 8:
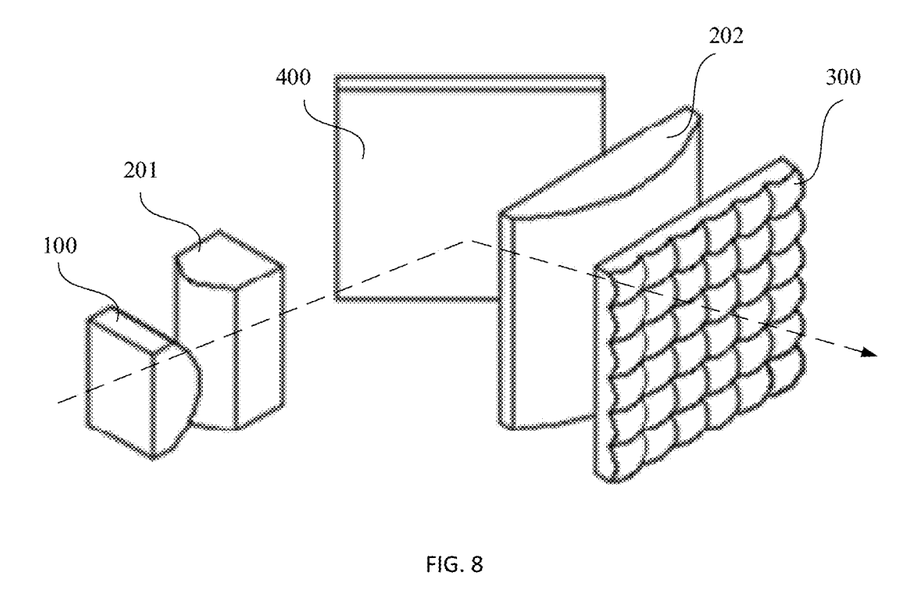
FIG. 8 is the third structural schematic diagram of the slow axis of the optical module provided by the embodiment of the present application.
Figure 9:
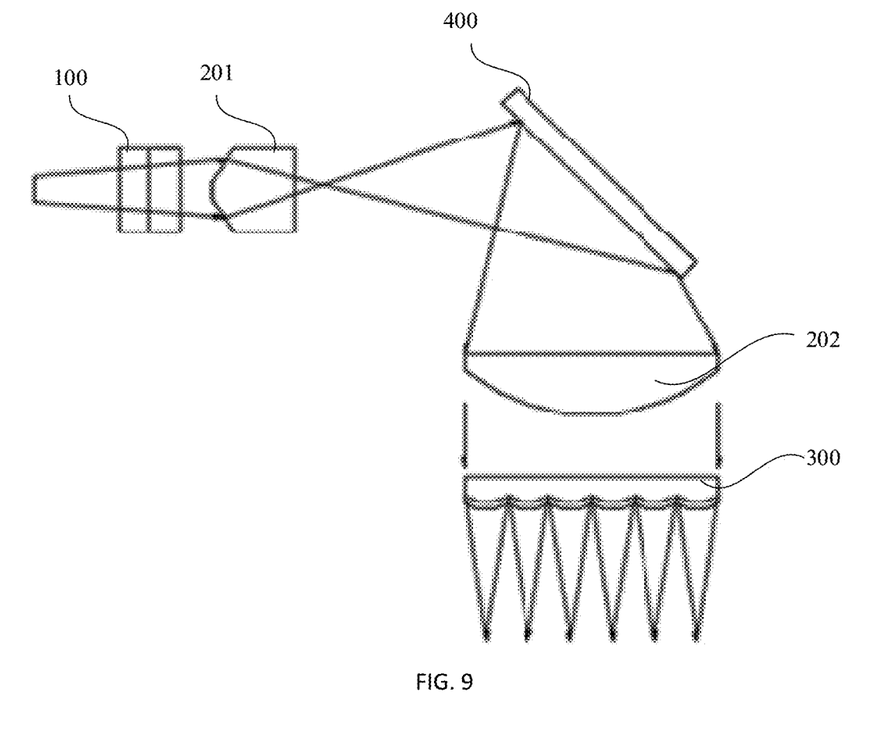
FIG. 9 is the second optical path diagram of the slow axis of the optical module provided by the embodiment of the present application.

A reflecting mirror 400 is also provided between the second lens 201 and the array lens 300. As shown in FIG. 8 and FIG. 9, when the third lens 202 is provided, the reflecting mirror 400 is located between the second lens 201 and the third lens 202. The reflecting mirror 400 can change the light exiting direction of the light.

When the reflecting mirror 400 does not rotate, the reflecting mirror 400 can change the light exiting direction of the light, and the light spot formed by it does not change.

The reflecting mirror 400 is rotatable along the main optical axis to scan the light spot, so as to change the light output range of the exiting surface of the array lens 300, so that the light spot has different variations, and the rotation angle of the reflecting mirror 400 is 0° to 90°, so as to continuously rotate and scan the light spot within the rotation angle.

For example, when the reflecting mirror 400 does not rotate, a strip-shape light spot or a point light spot can be formed as shown in FIG. 6. The exiting surface of the array lens 300 is formed of a plurality of first arc surfaces, which can form a strip-shape light spot. The exiting surface of the array lens 300, on the basis of the plurality of first arc surfaces, are also provided with a plurality of second arc surfaces, which can form the point light spot. At this time, the reflecting mirror 400 only changes the light exiting direction of the light, so that the position where the light spot is formed changes, but the shape of the formed light spot does not change.

Figure 10:
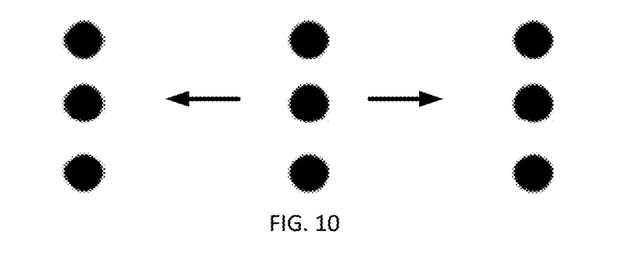
FIG. 10 is the fourth shape diagram of the slow axis output light spot of the optical module provided by the embodiment of the present application.
Figure 11:
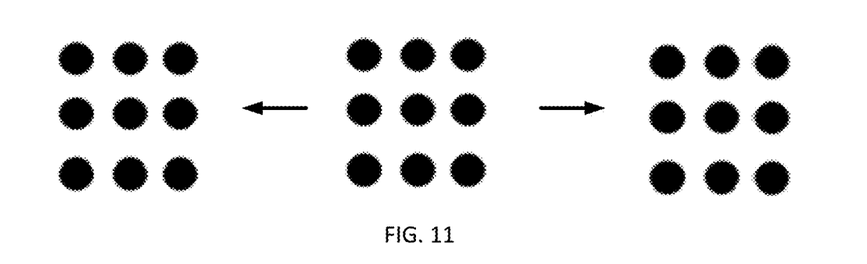
FIG. 11 is the fifth shape diagram of the slow axis output light spot of the optical module provided by the embodiment of the present application.
Figure 12:
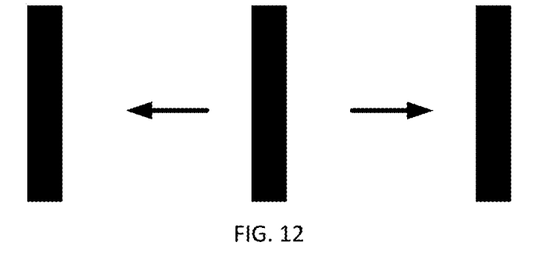
FIG. 12 is the sixth shape diagram of the slow axis output light spot of the optical module provided by the embodiment of the present application.
Figure 13:
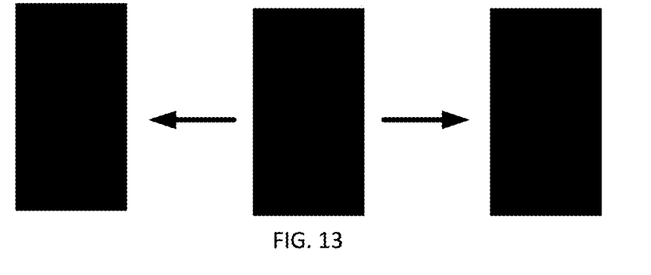
FIG. 13 is the seventh shape diagram of the slow axis output light spot of the optical module provided by the embodiment of the present application.

When the reflecting mirror 400 is rotated to scan, the reflecting mirror 400 can be rotated along the main optical axis to form a light spot in a larger range. For example, as shown in FIG. 10, the single-row point light spot spreads to the single-row point light spots on both sides, and finally an array-point light spot is formed. Alternatively, as shown in FIG. 12, the single-stripe light spot spreads to both sides, and finally the plural-stripe light spot is formed. When the rotation angle of the reflecting mirror 400 increases, it is formed that the array-point light spot, as shown in FIG. 11, spreads to both sides, forming an array-point light spot of the larger range. Alternatively, as shown in FIG. 13, the surface light spot spreads (is diffused) to the two sides to form the surface light spot of the larger area.

The larger the rotation angle of the reflecting mirror 400 is, the larger the light output range scanned by the reflecting mirror 400 is, and a light spot with more array points or a surface light spot with a larger area is more capable of being formed.

When the reflecting mirror 400 rotates, the light spot of a larger range is scanned to form light spots of different shapes. At this time, the distance between the first lens 100 and the light source may or may not be changed. When the distance between the first lens 100 and the light source does not change, the light spots of the wider range can be scanned only by rotating the reflecting mirror 400, to obtain the conversion of the light spot. When the distance between the first lens 100 and the light source changes, and the reflecting mirror 400 is still rotated, on the basis that the reflecting mirror 400 rotates to scan light spots of the larger range, because the distance between the first lens 100 and the light source is changed, the range of the output light spot is changed. The effect of the spot conversion finally formed is multiplied after the two work together, that is, there are more conversion forms of the light spots, and more types and shapes of light spots can be formed.

The converted light spot can also be formed by defocusing. Defocusing means that when the optical module is specifically applied to actual use, the light spot formed by the optical module acts on the working surface. The distance between the working surface and the focal point where the light spot is formed can be selected to form the conversion of the light spot. Using this (conversion) transformation of the light spots, the corresponding application is completed through the working surface.

To sum up, in order to output different light spots and achieve the purpose of converting the light spots, it is possible to change the distance between the first lens 100 and the light source (the movement variable N1), the shape of the exiting surface of the array lens 300 (the switching variable N2), defocus (the defocus variable N3) and the rotational scanning of the reflecting mirror 400 (the scanning variable N4), to form light spots with different variations.

The above-mentioned ways of converting light spots can be used alone or in combination. When used in combination, they can be partially or completely combined. When the above-mentioned ways of converting light spots are used in combination, the types of light spots to be converted=N1*N2*N3*N4.

For example, when the exiting surface of the array lens 300 is a grid-like protrusion as shown in FIG. 8, the row point light spot shown in FIG. 7 can be formed, and then the range of the formed row point light spot is changed by adjusting the distance between the first lens 100 and the light source, forming a single-row point or multi-row point as shown in FIG. 7, up to the array-point light spot.

The multi-row point light spot is an array light spot, and the row point light spot can be regarded as one kind of array-point light spot.

On this basis, the reflecting mirror 400 can also be rotated, and the reflecting mirror 400 is rotated to scan the formed light spot, so as to further change the light output range and form the conversion of the light spot.

As shown in FIG. 10 and FIG. 11, the range of the single-row point light spot or the array-point light spot can be further expanded to the rotation direction of the reflecting mirror 400, such as, forming a stripe-shape light spot. As shown in FIGS. 12 and 13, the range of the scanned stripe-shape light spot is further expanded.

To sum up, the shape of the light spot can be changed by means of changing the shape of the array lens 300, changing the distance between the first lens 100 and the light source, rotating the reflecting mirror 400 or defocusing. According to the above different combination manners, different light spots can be formed to achieve the purpose of converting the light spots, so that the formed light spots have diversification.

Figure 20:
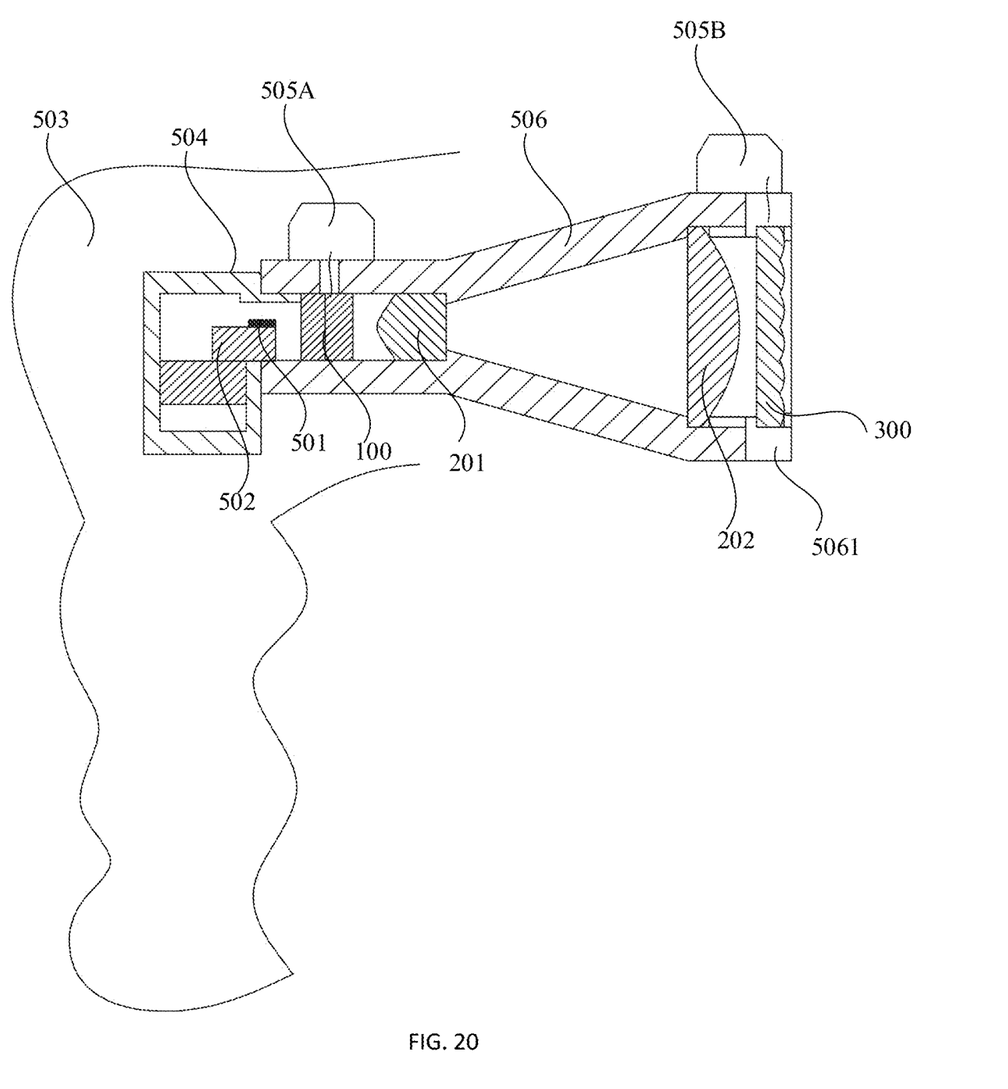
FIG. 20 is the first structural schematic diagram of a medical laser device provided by an embodiment of the present application.
Figure 21:
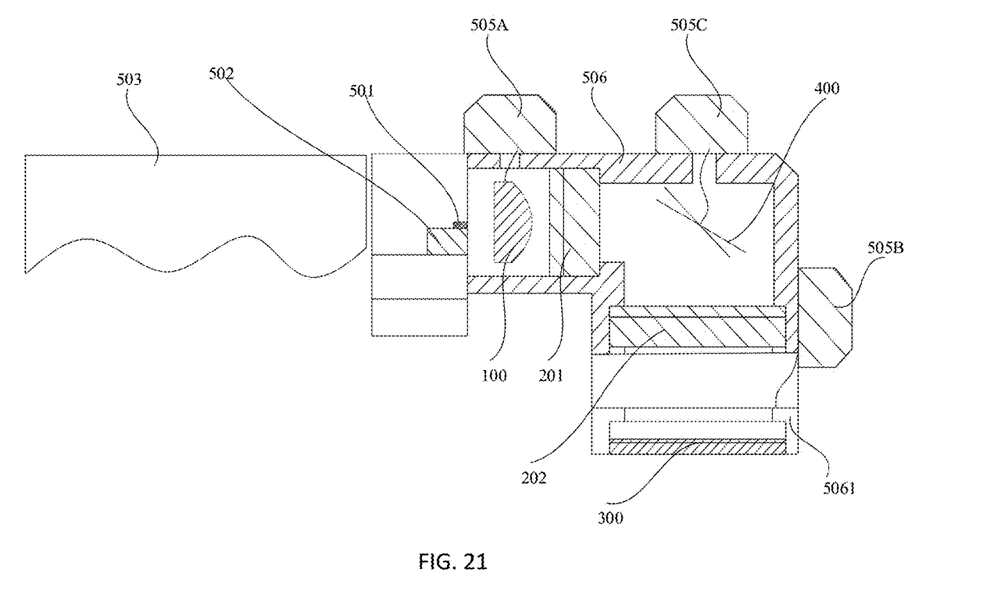
FIG. 21 is the second structural schematic diagram of a medical laser device provided by an embodiment of the present application.

When the above embodiments are applied to specific scenarios, such as, the medical industry, as shown in FIG. 20 and FIG. 21, this embodiment provides a medical laser device, including a casing, a laser 501 which is arranged in the casing, and an optical module of the above-mentioned embodiment which is arranged in the exiting direction of the laser 501.

A laser 501 is arranged in the casing, and the laser light emitted by the laser 501 is used as a light source. Through an optical module, a convertible light spot is emitted, and light spots of different shapes are applied to different treatments.

Specifically, the casing comprises a handle 503, a spacer 504 and a lens barrel 506. The handle 503 is convenient for the user to hold. The laser 501 is arranged in the spacer 504, the optical module is arranged in the lens barrel 506, and the lens barrel 506 and the spacer 504 are detachably connected.

The spacer 504 is provided therein with the heat sink 502, which is connected to the laser 501, to dissipate heat from the laser 501.

The detachable connection can facilitate the replacement of the lens barrel 506. In different lens barrels 506, it can correspond to different combinations in the optical module, such as, whether to provide the reflecting mirror 400 or the third lens 202.

Further, the front end of the lens barrel 506 is provided with a replaceable head 5061, the replaceable head 5061 is detachably connected to the lens barrel 506, and the array lens 300 is located in the replaceable head 5061, which also facilitate replacing the different array lens 300.

It also comprises a first motor 505A and a second motor 505B. The first motor 505A and the second motor 505B are respectively connected to the first lens 100 and the array lens 300. The first motor 505A drives the first lens 100 to move on the main optical axis, to change the distance between the first lens 100 and the laser 501. The second motor 505B drives the array lens 300 to translate.

As shown in FIG. 19, when the optical module comprises the reflecting mirror 400, it also comprises a third motor 505C, and the third motor 505C is connected to the reflecting mirror 400 to drive the reflecting mirror 400 to rotate.

As shown in FIG. 20, the light spot formed by the array lens 300 can be used for treatment and other work, and the distance between the working surface and the focal point of the array lens 300 can be adjusted.

Figure 22:
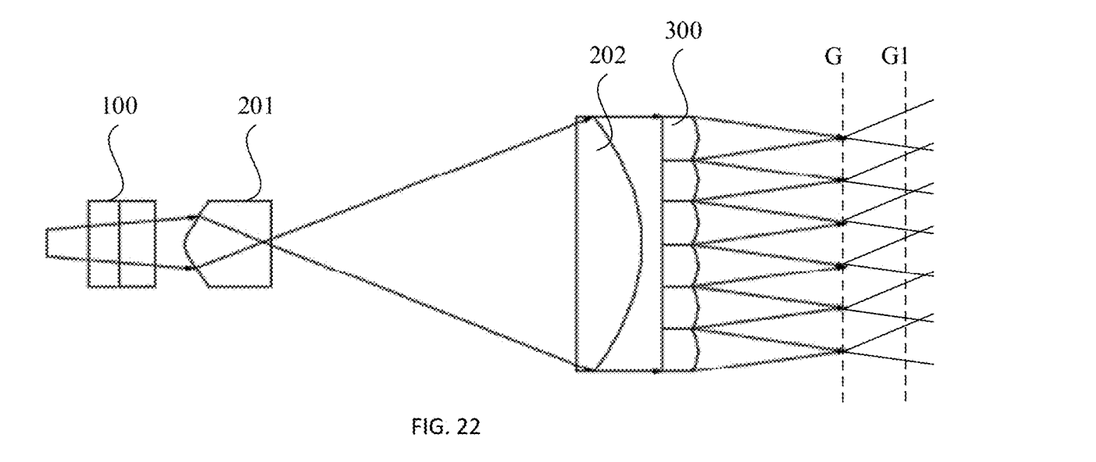
FIG. 22 is a defocus light path diagram of a slow axis of an optical module provided by an embodiment of the present application.

As shown in FIG. 22, when the working surface is at the focal position G of the array lens 300, skin rejuvenation treatment can be performed. When the working surface is far away from the focal position of the array lens 300, for example, at the G1 position, which is called as defocusing, the light spot formed at the defocusing position is different from that at the focal point, so that defocusing is another way of converting the light spot, and the hair removal treatment or the fat-dissolving treatment can be performed at the defocusing position.

The medical laser device comprises the structure and beneficial effects same as those in the foregoing embodiments. The structure and beneficial effects of the optical module have been described in detail in the foregoing embodiments, and not be repeated here.

Only preferred embodiments of the present application are provided above, and not intended to limit the present application. For those skilled in the art, the present application may have various modifications and changes. Any modifications, equivalent replacements or improvements, etc., made within the spirit and principle of the present application, shall be covered by the protection scope of the present application.

What is claimed is:

1. An optical module, comprising a first lens, a second lens and an array lens arranged in sequence along a main optical axis, wherein the first lens shapes a beam along a first direction of the main optical axis, the second lens shapes the beam along a second direction of the main optical axis, the array lens has an array arranged along the second direction of the main optical axis, and a laser beam enters the second lens after passing through the first lens, the second lens diffuses the laser beam along the second direction and converts the laser beam from a Gaussian distribution to a flat-top distribution in the second direction, and then the laser beam exits through the array lens, wherein the first direction and the second direction are perpendicular to each other.

2. The optical module according to claim 1, wherein the first lens is an ellipsoid lens, and the second lens is a hyperboloid lens.

3. The optical module according to claim 1, further comprising a third lens located between the second lens and the array lens, wherein the third lens shapes a beam along the second direction of the main optical axis.

4. The optical module according to claim 3, wherein a reflecting mirror is further provided between the second lens and the third lens.

5. The optical module according to claim 4, wherein the reflecting mirror is rotatable along the main optical axis, and a rotation angle of the reflecting mirror is 0°-90°, so as to scan a light spot within the rotation angle.

6. The optical module according to claim 1, wherein the array lens comprises a plurality of first arc surfaces or a sawtooth surface continuously formed along the second direction, and the first arc surfaces or the sawtooth surface are located on an incident surface or an exiting surface of the array lens.

7. The optical module according to claim 6, wherein the incident surface of the array lens is a flat surface, a convex surface or a concave surface, and the exiting surface of the array lens is formed of a plurality of the first arc surfaces or the sawtooth surface; or, the incident surface of the array lens is formed of a plurality of the first arc surfaces or the sawtooth surface, and the exiting surface of the array lens is a flat surface, a convex surface or a concave surface.

8. The optical module according to claim 6, wherein the array lens further comprises a plurality of second arc surfaces or a sawtooth surface arranged along the first direction, and the second arc surfaces or the sawtooth surface are located on the incident surface or the exiting surface of the array lens.

9. The optical module according to claim 8, wherein the incident surface or the exiting surface of the array lens comprises a plurality of first arc surfaces continuously formed along the second direction, and the incident surface or the exiting surface of the array lens further comprises a plurality of second arc surfaces continuously arranged along the first direction on a basis of a plurality of the first arc surfaces; or
the incident surface of the array lens is a sawtooth surface arranged along the first direction, and the exiting surface of the array lens is formed of a plurality of the first arc surfaces arranged along the second direction; or
the incident surface of the array lens is formed of a plurality of the first arc surfaces arranged along the second direction, and the exiting surface of the array lens is a sawtooth surface arranged along the first direction; or
the incident surface of the array lens is a sawtooth surface, and the exiting surface of the array lens is a sawtooth surface.

10. The optical module according to claim 8, wherein the array lens comprises a first array lens and a second array lens, and the first arc surfaces or the sawtooth surface are located on an incident surface or an exiting surface of the first array lens, and/or an incident surface or an exiting surface of the second array lens.

11. The optical module according to claim 6, wherein the array lens can reciprocate along a sawtooth arrangement direction, or rotate along a direction of the main optical axis.

12. The optical module according to claim 6, wherein tooth surfaces of the sawtooth have curvature.

13. The optical module according to claim 1, wherein the array lens is an array reflecting mirror, and a plurality of first arc surfaces or sawtooth disposed along the second direction are continuously formed on a reflecting surface of the array reflecting mirror.

14. The optical module according to claim 13, wherein the array lens can reciprocate along a sawtooth arrangement direction, or rotate along a direction of the main optical axis.

15. The optical module according to claim 13, wherein tooth surfaces of the sawtooth have curvature.

16. The optical module according to claim 1, wherein the first lens is movable along a direction of the main optical axis, to change a light output range of an exiting surface of the array lens.

17. A medical laser device, comprising a casing which is therein provided with a laser and the optical module according to claim 1, which is arranged in an exiting direction of the laser.

18. The medical laser device according to claim 17, wherein the casing comprises a handle and a lens barrel, the laser is arranged in the handle, the optical module is arranged in the lens barrel, the lens barrel and the handle are detachably connected with each other; and the lens barrel comprises a replaceable head, the array lens is located in the replaceable head, and the replaceable head and the lens barrel are detachably connected.

19. The medical laser device according to claim 17, further comprising a first motor and/or a second motor, wherein the first motor and the second motor are respectively connected to the first lens and the array lens.

* * * * *